(12) United States Patent
Bergen-Brenkman et al.

(10) Patent No.: US 8,796,480 B2
(45) Date of Patent: Aug. 5, 2014

(54) PROCESS FOR PRODUCING MONOBRANCHED FATTY ACIDS OR ALKYL ESTERS

(75) Inventors: Tanja Van Bergen-Brenkman, Gouda (NL); Hans Ridderikhoff, Gouda (NL); Hendrikus Johannes Franciskus Philipse, Heteren (NL)

(73) Assignee: Croda International PLC, East Yorkshire (GB)

( * ) Notice: Subject to any disclaimer, the term of this patent is extended or adjusted under 35 U.S.C. 154(b) by 0 days.

(21) Appl. No.: 14/110,806

(22) PCT Filed: Apr. 17, 2012

(86) PCT No.: PCT/GB2012/050841
§ 371 (c)(1),
(2), (4) Date: Oct. 9, 2013

(87) PCT Pub. No.: WO2012/146909
PCT Pub. Date: Nov. 1, 2012

(65) Prior Publication Data
US 2014/0031571 A1   Jan. 30, 2014

(30) Foreign Application Priority Data

Apr. 28, 2011   (GB) .................................. 1107198.2
Sep. 12, 2011   (GB) .................................. 1115727.8

(51) Int. Cl.
*C07C 51/00* (2006.01)

(52) U.S. Cl.
USPC .......................................... 554/163; 554/161

(58) Field of Classification Search
USPC ................................................. 554/161, 163
See application file for complete search history.

(56) References Cited

U.S. PATENT DOCUMENTS

| | | | |
|---|---|---|---|
| 3,346,510 A | 10/1967 | Sinfelt et al. | |
| 4,371,469 A | 2/1983 | Foglia et al. | |
| 4,490,480 A | 12/1984 | Lok et al. | |
| 5,364,949 A | 11/1994 | Neuss et al. | |
| 5,463,160 A | 10/1995 | Kuhlmann et al. | |
| 5,648,584 A | 7/1997 | Murray | |
| 5,677,473 A * | 10/1997 | Tomifuji et al. | 554/158 |
| 2004/0204598 A1 | 10/2004 | Zhang et al. | |
| 2011/0263884 A1 | 10/2011 | Ngo et al. | |
| 2011/0275844 A1 | 11/2011 | Ngo et al. | |

FOREIGN PATENT DOCUMENTS

| | | |
|---|---|---|
| EP | 0167201 | 1/1986 |
| EP | 0168091 | 1/1986 |
| EP | 0353915 | 8/1988 |
| EP | 0415697 | 3/1991 |
| EP | 0683150 | 11/1995 |
| GB | 1178186 | 1/1970 |
| WO | WO 91/06367 | 5/1991 |
| WO | WO 2011/136903 | 11/2011 |

OTHER PUBLICATIONS

International Written Opinion for PCT/GB2012/050841, Authorized Officer of EPO, Miriam Adechy, Issued Oct. 29, 2013.
Shokubai Koza, vol. 10, Edited by the Catalysis Society of Japan, Kodansha Ltd. (1986).
Meier, WM; Olson, DH; Baerlocher, CH, "Atlas of Zeolite Structure Types", 4th Revised Ed.; Elsevier; London, 1996; p. 106.
International Search Report for PCT/GB2012/050841, Authorized Officer of EPO, Miriam Adechy, Issued Aug. 10, 212.
Anonymous Third Party Observation for PCT/GB2012/050841, Issued May 20, 2013.

* cited by examiner

*Primary Examiner* — Deborah D Carr
(74) *Attorney, Agent, or Firm* — RatnerPrestia

(57) ABSTRACT

A process for producing $C_{10}$-$C_{26}$ monobranched fatty acids or alkyl esters thereof which includes isomerizing unsaturated $C_{10}$-$C_{26}$ fatty acids or alkyl esters thereof in the presence of a catalyst which comprises both a zeolite and a Lewis base. The zeolite can be reused after simple separation from the reaction products without having to regenerate. The process is particularly suitable for producing highly monobranched fatty acids or alkyl esters thereof.

15 Claims, No Drawings

PROCESS FOR PRODUCING MONOBRANCHED FATTY ACIDS OR ALKYL ESTERS

CROSS REFERENCE TO RELATED APPLICATIONS

This application is the U.S. National Phase application of PCT International Application No. PCT/GB2012/050841, filed Apr. 17, 2012, and claims priority of British Patent Application No. 1107198.2, filed Apr. 28, 2011, and British Patent Application No. 1115727.8, filed Sep. 12, 2011, the disclosures of which are incorporated herein by reference in their entireties for all purposes.

FIELD OF INVENTION

The present invention relates to a process for producing monobranched fatty acids or alkyl esters thereof, and in particular highly monobranched fatty acids or alkyl esters thereof.

BACKGROUND

Fatty acids are versatile building blocks used in many parts of the chemical industry, in applications ranging from lubricants, polymers, and solvents to cosmetics and health care. Fatty acids are generally obtained by the hydrolysis of triglycerides of vegetable or animal origin. Naturally occurring triglycerides are esters of glycerol and generally straight chain, even numbered carboxylic acids, ranging from 10 to 24 carbon atoms. Most common are fatty acids having 12, 14, 16 or 18 carbon atoms. The fatty acids can be either saturated or contain one or more unsaturated carbon bonds.

Straight chain saturated fatty acids having 10 or more carbon atoms are solid at room temperature, which makes them difficult to process in a number of applications. Unsaturated long chain fatty acids, e.g. oleic acid, are liquid at room temperature, and so are easy to process, but are unstable because of the existence of one or more double bonds. Branched fatty acids can mimic the properties of the straight chain unsaturated fatty acids in many respects. However, they do not have the disadvantage of being unstable. Thus, branched fatty acids are, for many applications, more desirable than straight chain fatty acids. The branched fatty acids have alkyl side groups which are generally short, e.g. methyl, ethyl or propyl, and can be attached to the carbon chain backbone at any position.

Commercially available branched fatty acids such as isostearic acid, are obtained as a by-product of the catalytic or thermal dimerisation of unsaturated straight chain fatty acids. Isostearic acid is produced by heating oleic acid in the presence of catalyst, generally clay, to produce dimer, trimer and higher oligomer acids. But instead of polymerising, a portion of the oleic acid rearranges to give a branched, monomeric fatty acid which can be isolated by distillation and hydrogenated. This saturated branched monomeric fatty acid is a mixture of various linear and mainly branched, both mono and poly branched, saturated acids which is known as isostearic acid.

Isostearic acid exhibits better stability to oxidation than oleic acid, and is a very useful product which is sold into a wide range of application areas such as lubricant esters, and cosmetic applications. Isostearic acid is also used to make isostearyl alcohol.

The dimerisation process only produces about 20 to 40% by weight of isostearic acid, and thus there is a need for a more efficient process. A further disadvantage, which increases the cost of the process, is that the clay catalyst cannot be reused.

EP-0683150 describes an alternative process for producing branched fatty acids by using a zeolite catalyst which has a linear pore structure. This process has a much higher selectivity towards monomeric than dimeric or oligomeric products.

Isostearic acid can be further purified, e.g. as described in EP-0415697, using urea clathration. But this additional processing stage increases the overall cost of the process.

Thus, there is a need for an improved process of producing monobranched fatty acids, particularly highly monobranched fatty acids.

SUMMARY OF THE INVENTION

We have now discovered a process for producing monobranched fatty acids which reduces or substantially overcomes at least one of the aforementioned problems. Accordingly, the present invention provides a process for producing monobranched fatty acids or alkyl esters thereof which comprises;

(A) (i) isomerising unsaturated $C_{10}$-$C_{26}$ fatty acids or alkyl esters thereof in the presence of a catalyst which comprises both a zeolite and a Lewis base,
  (ii) separating the reaction product of step (i) from the used zeolite,
  (iii) optionally hydrogenating the reaction product of step (ii),
  (iv) obtaining a composition comprising monobranched $C_{10}$-$C_{26}$ fatty acids or alkyl esters thereof from the reaction product of step (ii) or (iii), and (B) wherein the process steps (A)(i) to (iv) are repeated using zeolite which comprises used zeolite which has been obtained in step (A)(ii).

The invention also provides a composition comprising (i) greater than 70% by weight of monobranched $C_{10}$-$C_{26}$ fatty acids or alkyl esters thereof, (ii) less than 7% by weight of polybranched $C_{10}$-$C_{26}$ fatty acids or alkyl esters thereof, (iii) greater than 3% by weight of linear $C_{10}$-$C_{26}$ fatty acids or alkyl esters thereof, and (iv) less than 5% by weight of lactones, all based on the total weight of the composition.

The invention further provides the use of a catalyst which comprises both a zeolite and a Lewis base in the isomerisation of unsaturated $C_{10}$-$C_{26}$ fatty acids or alkyl esters thereof to produce highly monobranched $C_{10}$-$C_{26}$ fatty acids or alkyl esters thereof.

The invention still further provides the reuse of a zeolite in combination with a Lewis base to obtain a steady state process for producing $C_{10}$-$C_{26}$ monobranched fatty acids or alkyl esters thereof.

DETAILED DESCRIPTION OF THE INVENTION

The raw materials for the unsaturated fatty acids or alkyl esters thereof starting material used in the present invention are preferably naturally occurring materials such as triglyceride oils and can be of animal (e.g. tallow), or preferably of vegetable origin. Suitable fatty acids include sunflower fatty acids, soybean fatty acids, olive fatty acids, rapeseed fatty acids, linseed fatty acids, cottonseed fatty acids, safflower fatty acids, tall oil fatty acids and tallow olein. Relatively pure unsaturated fatty acids such as oleic acid, linoleic acid, linolenic acid, palmitoleic acid, and elaidic acid may be isolated and used, or relatively crude unsaturated fatty acid mixtures employed.

References to fatty acids described herein also include the alkyl esters thereof. Thus, alkyl esters of the unsaturated fatty acids herein described having a total carbon number of 10 to 26 may be used as the starting material. Although the alkyl moiety may be up to half of the total carbon number, normally it will be 1 to 3, preferably 1 carbon atom(s). Specific examples of alkyl esters include methyl esters, ethyl esters and propyl esters of unsaturated fatty acids, with methyl esters being preferred.

When a mixture of alkyl esters is used as the starting material, the mixture contains at least one alkyl ester of the herein described unsaturated fatty acids. Specifically, it is a mixture of one or more alkyl esters of these unsaturated fatty acids, or a mixture containing at least one alkyl ester of these unsaturated fatty acids and saturated fatty acids. In the case of a mixture, the content of alkyl esters of the herein described unsaturated fatty acids is preferably greater than 50% by weight, more preferably greater than 80% by weight, and especially greater than 90% by weight.

The unsaturated fatty acids starting material suitably comprises $C_{12}$-$C_{24}$ fatty acids, preferably $C_{14}$-$C_{22}$ fatty acids, more preferably $C_{16}$-$C_{22}$ fatty acids, particularly $C_{18}$ or $C_{22}$ fatty acids, and especially $C_{18}$ fatty acids. The fatty acids starting material suitably comprises greater than 70%, preferably greater than 80%, more preferably greater than 90%, particularly greater than 95%, and especially greater than 97% by weight of fatty acids falling within the aforementioned carbon chain ranges or number, based on the total weight of fatty acids present.

The unsaturated fatty acids starting material suitably comprises (i) greater than 70%, preferably greater than 80%, more preferably in the range from 90 to 99.9%, particularly 95 to 99.5%, and especially 97 to 99% by weight of unsaturated fatty acids; and/or (ii) less than 30%, preferably less than 20%, %, more preferably in the range from 0.1 to 10%, particularly 0.5 to 5%, and especially 1 to 3% by weight of saturated fatty acids, both based on the total weight of fatty acids present.

The unsaturated fatty acid component comprises at least one ethylenic double bond, but may comprise two or even three double bonds. The unsaturated fatty acid component suitably comprises (i) greater than 50%, preferably greater than 60%, more preferably in the range from 80 to 100%, particularly 90 to 99%, and especially 95 to 98%, by weight of fatty acids having one double bond; and/or (ii) less than 50%, preferably less than 40%, more preferably in the range from 0 to 20%, particularly 1 to 10%, and especially 2 to 5% by weight of fatty acids having 2 double bonds, both based on the total weight of unsaturated fatty acids present.

The isomerisation catalyst used in the present invention is a combination of both a zeolite and a Lewis base.

The zeolite is suitably used at a concentration of less than 10%, preferably less than 5%, more preferably in the range from 0.1 to 3%, particularly 0.5 to 2.5%, and especially 1 to 2% by weight based on the weight of fatty acids starting material.

The Lewis base is suitably used at a concentration of less than 2%, preferably less than 1%, more preferably in the range from 0.01 to 0.5%, particularly 0.02 to 0.1%, and especially 0.03 to 0.05% by weight based on the weight of fatty acids starting material.

The ratio by weight of zeolite to Lewis base used is suitably greater than 5:1, preferably in the range from 10 to 100:1, more 20 to 70:1, preferably particularly 30 to 50:1, and especially 35 to 45:1.

One advantage of the present invention is that the zeolite can be directly reused many times, without being subjected to regeneration. By "reused" is meant used again as a catalyst after one or more reaction cycles without being subjected to regeneration. By "regeneration" is meant isolation of the zeolite followed by treatments such as washing with solvent, and/or heating, for example, in an inert atmosphere or acid solution, and drying.

In a preferred embodiment of the present invention, the zeolite allows multiple reuse after simple separation from the reaction products, e.g. by filtration or centrifugation. Surprisingly little loss of the zeolite activity occurs on reuse. Thus, the zeolite may be suitably reused once, preferably 2 or more times, more preferably 3 or more times, especially 4 or more times, and particularly 5 or more times. We have surprisingly found that after 2 zeolite reuses (three reaction cycles) a steady state can be effectively achieved which enables almost infinite or continuous reuse, i.e. can be used in a batch or a continuous process. The steady state is shown by the retention of catalyst activity.

Thus, the zeolite catalyst preferably retains at least 90%, more preferably at least 95%, particularly at least 97%, and especially at least 99% of its activity after the third, preferably the fourth, more preferably the fifth, particularly the sixth, and especially after further subsequent reuses.

Zeolite activity (measured in the presence of Lewis base) is determined as described herein. Loss of activity of the reused zeolite is measured as the increase in time required to achieve the same degree of conversion as obtained for the second reuse of the zeolite. Zeolite activity is expressed as the percentage retention of activity. 100% retention of activity means that the same degree of conversion occurred during the same time period as for the second reuse of the zeolite.

In one embodiment, the zeolite is reused without the addition of any, or significant quantities, of fresh (unused) or regenerated zeolite. Thus, after the first reaction cycle, the zeolite catalyst employed suitably comprises (i) greater than 95%, preferably greater than 96%, more preferably greater than 97%, particularly greater than 98%, and especially greater than 99% by weight of used catalyst; and/or (ii) less than 5%, preferably less than 4%, more preferably less than 3%, particularly less than 2%, and especially less than 1% by weight of fresh or regenerated zeolite, both based on the total (dry) weight of zeolite present.

In normal processing, some of the zeolite catalyst will be lost during recovery and therefore fresh or regenerated zeolite will need to be added to the reused catalyst to maintain the zeolite concentration. Thus, after the first reaction cycle, the zeolite catalyst employed suitably comprises (i) 95% or less, preferably 90% or less, more preferably in the range from 70 to 86%, particularly 75 to 84%, and especially 78 to 82% by weight of used catalyst; and/or (ii) 5% or greater, preferably 10% or greater, more preferably in the range from 14 to 30%, particularly 16 to 25%, and especially 18 to 22% by weight of fresh or regenerated zeolite, both based on the total (dry) weight of zeolite present.

Our experiments have shown that the Lewis base is lost from the reaction mixture when the monobranched fatty acids product is removed. Thus, it would be expected that similar quantities of Lewis base would need to be added for each reaction cycle. However, we have surprisingly shown that significant improvements in conversion rate and/or yield and/or reduction in the time of the reaction can occur when much lower quantities of Lewis base are added to the reused zeolite, i.e. when the Lewis base is used at a much lower concentration than with fresh or regenerated zeolite. Thus, the same amount of Lewis base may be added to the reused zeolite, but in one preferred embodiment less Lewis base is used, suitably less than 80%, preferably less than 60%, more preferably in the range from 5 to 45%, particularly 10 to 35%, and especially 15 to 25% by weight of the original amount used with the fresh or regenerated zeolite in the first reaction cycle. The ratio of the amount of Lewis base used with fresh or regenerated zeolite to reused zeolite is suitably greater than 1.5:1, preferably in the range from 2 to 20:1, more preferably 3 to 10:1, particularly 4 to 5.5:1, and especially 4.5 to 5:1.

In one embodiment, the isomerisation reaction suitably occurs over a time period of 0.5 to 16 hours, preferably 1 to 12 hours, more preferably 2 to 10 hours, particularly 3 to 8 hours, and especially 4 to 6 hours.

The isomerization reaction is preferably carried out at 150 to 350° C., more preferably 200 to 300° C., particularly 225 to 280° C., and especially 250 to 270° C. The reaction may be carried out in a closed system, such as an autoclave, where the system can be pressurized. A suitable pressure is 2 to 50 kgf/cm$^2$. The reaction mixture may be flushed out, and pressurized, with a gas such as nitrogen or hydrogen, preferably nitrogen. The use of a closed system will prevent vaporization of water, alcohols and any other low boiling substances in the system, including any contained in the catalyst.

The zeolite isomerisation catalyst used in the present invention is a crystalline aluminosilicate, which preferably has the general formula $M^{n+}_{x/n}[AlO_2)_x(SiO_2)_{y(y>x)}]\cdot zH_2O$, where M is a metal cation of groups IA (including hydrogen) or IIA, and n is the valency of the metal. The zeolite suitably comprises a microporous network of $SiO_4$ and $AlO_4$ tetrahedra linked together via shared oxygen atoms. The aluminum preferably has a 3+ valency resulting in an excess negative charge on the $AlO_4$ tetrahedra, which can be compensated by $H^+$ or other cations, e.g. $Na^+$, $NH_4^+$, $Ca^{2+}$. When M is hydrogen, the materials are Bronsted acidic, whereas when M is, for example, caesium, the materials are basic. Upon heating, Bronsted acidic hydroxyls condense creating coordinately unsaturated Al, which acts as a Lewis acid site. The acid strength, acid site density and Bronsted versus Lewis acidity are determined by the level of framework aluminium. The ratio of silica/alumina can be varied for a given class of zeolites either by controlled calcination, with or without the presence of steam, optionally followed by extraction of the resulting extraframework aluminium, or by chemical treatment employing, for example, ammonium hexafluorosilicate. The zeolite used in the present invention preferably has a silica/alumina ratio in the range from 3 to 300, more preferably 5 to 200, and particularly 10 to 100. The ratio can be easily determined by atomic absorption photometry.

In one embodiment, the zeolite catalyst has a "linear pore structure", wherein pores are formed by at least linear continuous pathways. In addition, the zeolite preferably has pores which are small enough to retard dimerisation and coke formation within the pore structure, and large enough to allow diffusion of branched chain fatty acids or esters thereof out of the pores. The mean pore size of the largest channels of the zeolite is preferably in the range from 4 to 9 Angstrom, and more preferably 4 to 7 Angstrom. The zeolite preferably does not have additional larger cavities. Such zeolites belong to the "medium or intermediate pore size zeolites" and examples include ferrierite, stilbite, mordenite and/or beta, L type zeolites. Suitable commercially available zeolites include ZSM-22, ZSM-23, ZSM-35, ZSM-5, ZSM-11, ZSM-57, and ZSM-12.

One suitable type of zeolite possess a unidimensional pore topology, such as mordenite. The mordenite type zeolite, the highest in silicon content among naturally-occurring zeolites, is a zeolite composed of oxygen 12-membered ring wherein the pores are formed mainly by tunnel-like pore pathways (Shokubai Koza, Vol. 10, edited by the Catalysis Society of Japan, Kodansha Ltd. (1986)).

Commercial products of the mordenite type include the HSZ-600 series products, such as HSZ-620HOA, HSZ-640HOA and HSZ-690HOA (ex Tosoh Corporation). Another suitable type of zeolite belong to the classes of zeolite L and zeolite omega. Zeolite L is described in WO 91/06367, and zeolite omega is described in GB-1178186.

In addition to pore topology, the morphology and/or crystallite size of the zeolite material may also be important. The crystallite morphology can be accurately quantified by measuring the crystallite diameter and the crystallite depth, e.g. the maximum crystallite diameter (L) and the maximum crystallite depth (D). These can be measured using a combination of scanning electron microscopy (SEM) and/or transmission electron microscopy (TEM), e.g. as described in WO 91/06367. The L/D ratio (crystallite aspect ratio) is preferably greater than 8, more preferably greater than 10, particularly in the range from 15 to 40, and especially 20 to 30.

One particularly suitable type of zeolite comprises channels of ten-membered rings (10-MR) in one direction, and nine-or-less-membered ring intersecting channels in the other directions (as described in U.S. Pat. No. 5,463,160), such as ZSM-35 (U.S. Pat. No. 5,648,584), SUZ-4 (EP-0353915), and ferrierite. In such zeolite catalysts, there are no extra cavities at the intersections. The ferrierite is characterised by a two dimensional pore system consisting of 10-MR channels parallel to [001] interconnected with 8-MR channels parallel to [010]. Additionally, small channels formed by six-membered rings are present. Both 10-MR and 8-MR channels are elliptical in shape with dimentions of 4.2×5.4 Angstroms and 3.5×4.8 Angstroms, respectively (see Meier, W M; Olson, D H; Baerlocher, Ch, Atlas of Zeolite Structure Types, 4$^{th}$ revised ed.; Elsevier; London, 1996; p106). Suitable commercially available ferrierite includes K-Ferrierite HSZ-720 KOA (ex Tosoh Corporation) which has a silica/alumina ratio of 17.5, and Ferrierite CP914C (NH4+ form, ex Zeolyst).

In addition, zeolites with structures close to the above preferred class may be converted to the desired pore structures using methods known to those skilled in the art. For example, zeolites having channels with smaller pore size can be enlarged by replacing alkali (earth) metals by hydrogen; and alternatively, zeolites with larger pore size can be reduced by substituting the alkali metals with larger ions such as larger alkaline earth metals.

Although it is preferable from the viewpoint of catalyst activity that the cation in the zeolite is a proton, a zeolite of the potassium, ammonium or similar type, may be used after being converted into the proton type by suitable ion exchange.

The isomerisation reaction may be carried out in the presence of water or a lower alcohol. This is to suppress acid anhydride formation due to dehydration or dealcoholation of the starting material. This suppression is attributable to acid point modification of zeolite, such as conversion of Lewis acid point into Bronsted acid point. It is preferable to add water when the starting material is unsaturated fatty acids; and an alcohol when the starting material is esters of unsaturated fatty acids. The lower alcohol used suitably comprises 1 to 3 carbon atoms, with methanol, ethanol, and propanol being preferred. The lower alcohol preferably has the same alkyl group as that of the fatty acid ester starting material.

The Lewis base used in the present invention is preferably of sufficient size that it cannot enter the internal pore structure of the zeolite (e.g. for ferrierite, 3.5×4.8 Angstroms for the 8-MR channels). The Lewis base preferably comprises at least one heteroatom such as a nitrogen, phosphorus, oxygen or sulphur atom, more preferably a nitrogen or phosphorus atom, and particularly a phosphorus atom. The Lewis base may be any suitable amine or phosphine, particularly an organoamine or organophosphine.

The organoamine may be a monoamine, diamine or triamine and/or an alkyl, cycloalkyl, aryl or alkylarylamine, e.g. an alkylamine, dialkylamine, trialkylamine, arylamine, diarylamine, triarylamine, alkylarylamine, and/or dialkylarylamine. The amine may also be a nitrogen containing alkaloid such as a pyridine derivative, tropane derivative, pyrrolizidine derivative, piperidine drivative, quinolizidine derivative, pyrrolidine derivative, indolizidine derivative, isoquinoline derivative, oxazole derivative, isoxazole derivative, thiazole derivative, quinazoline derivative, acrine derivative, quinoline derivative, indole derivative, imidazole derivative, purine derivatives, and mixtures thereof.

The alkyl and/or aryl group of the amine preferably comprises 1 to 10, more preferably 1 to 6, and particularly 1 to 3 carbon atoms. The organoamine may be dimethylamine, trimethylamine, diethylamine, triethylamine, propylamine, dipropylamine, tripropylamine, phenylamine, diphenylamine, triphenylamine. pyridine, piperidine, quinuclidine, 2,6-lutidine, 2,2'-bipyridine, 1,4-diazabicyclo[2.2.2]octane, tropane, 1,10-phenanthroline, tetramethylethylenediamine and mixtures thereof.

The organophosphine may be a monophosphine, diphospine, triphosphine or cyclic phosphine and/or an alkyl, aryl or alkylarylphosphine. The organophosphine may be an alkylphosphine, dialkylphosphine, trialkylphosphine, arylphosphine, diarylphosphine, triarylphosphine, alkylarylphosphine, dialkylarylphosphine, and/or alkyldiarylphosphine. The alkyl group of the phosphine preferably comprises 1 to 10, more preferably 1 to 6, and particularly 1 to 3 carbon atoms. The aryl group of the phosphine preferably comprises 6 to 14, more preferably 6 to 8, and particularly 6 carbon atoms.

The arylphosphine may be phenylphosphine, diphenylphosphine, triphenylphosphine, tolylphosphine, ditolylphosphine, tritolylphosphine, xylylphosphine, dixylylphosphine, trixylylphosphine, 2,2'-bis(diphenylphosphino)-1,1'-binaphthyl, and/or tri(1-naphthyl)posphine.

The alkylphosphine may be methylphosphine, ethylphosphine, propylphosphine, butylphosphine, pentylphosphine, hexylphosphine, heptylphosphine, octylphosphine, cyclopentylphosphine and/or cyclohexylphosphine. The dialkyl and trialkylphosphine may be formed from any one or more of the aforementioned alkyl substituents. In a preferred embodiment, the same alkyl substituent is present for the dialkyl or trialkylphosphine. Thus, preferred dialkylphosphines include dimethylphosphine, diethylphosphine, dipropylphosphine, dibutylphosphine, dipentylphosphine, dihexylphosphine, diheptylphosphine, dioctylphosphine, dicyclopentylphosphine, dicyclohexylphosphine, and/or di-t-butylphosphine. Similarly, preferred trialkylphosphines include trimethylphosphine, triethylphosphine, tripropylphosphine, triisopropyl, tributylphosphine, triisobutylphosphine, tripentylphosphine, trihexylphosphine, triheptylphosphine, trioctylphosphine, tricyclopentylphosphine, and/or tricyclohexylphosphine.

The alkylarylphosphine, dialkylarylphosphine, and/or alkyldiarylphosphine may comprise any one or more of the aforementioned alkyl and aryl substituents. Suitable examples include dibutylphenylphosphine, dicyclohexylphenylphosphine.

Suitable diphosphines include 1,1-Bis(diphenylphosphino)methane, 1,2-Bis(dimethylphosphino)ethane, 1,2-Bis (diisopropylphosphino)ethane, dimer of phenylanisylmethylphosphine, 1,3-Bis(diphenylphosphino)propane, 1,4-Bis (diphenylphosphino)butane, 2,3-Bis(diphenylphosphino) butane, 2,2'-bis(diphenylphosphino)-1,1'-binaphthyl, 4,5-Bis (diphenylphosphino)-9,9-dimethylxanthene, 4,4,4',4',6,6'-Hexamethyl-2,2'-spirobichromane-8,8'-diylbis (diphenylphosphane), 4,4'-Bi-1,3-benzodioxole-5,5'-diylbis (diphenylphosphane), 1,1'-Bis(diphenylphosphino) ferrocene, and 1,2-Bis(2,5-dimethylphospholano)benzene. A preferred triphosphine is Bis(diphenylphosphinoethyl)phenylphosphine).

In a particularly preferred embodiment, the organophosphine is an arylphosphine, more preferably a triarylphosphine as described herein, and especially triphenylphosphine.

The product obtained from the isomerization reaction comprises high concentrations (suitably greater than 75 wt %, preferably greater than 80 wt %) of branched chain unsaturated fatty acids, or esters thereof. The product also comprises relatively low concentrations (suitably less than 10 wt %, preferably less than 5 wt %) of polymeric fatty acids such as dimer acid and trimer acid, and these can be removed, for example by vacuum distillation at a suitable temperature, for example up to 230° C. Where a hydrogenation step is employed, the polymeric fatty acids may be removed after hydrogenation.

The conversion rate, i.e. % by weight of unsaturated fatty acid starting material which is reacted, in the process of the present invention is suitably greater than 90%, preferably greater than 93%, more preferably greater than 95%, particularly in the range from 96 to 99%, and especially 97 to 98% by weight.

The zeolite catalyst can be separated from the reaction product of the isomerisation reaction, for example by filtration, preferably using a pressurized filtration unit with carton depth filter, and then reused as described herein.

The reaction product of the isomerisation reaction is suitably hydrogenated in an autoclave by a known method, such as the method using a standard hydrogenation catalyst, particularly a metal hydrogenation catalyst. Catalysts for hydrogenation are well known and can be homogeneous or heterogeneous (e.g. present in a different phase, typically the solid phase, than the substrate). Other useful hydrogenation catalysts include nickel, copper, palladium, platinum, molybdenum, iron, ruthenium, osmium, rhodium, iridium, zinc or cobalt, and particularly zinc. Combinations of catalysts can also be used. Bimetallic catalysts can be used, for example, palladium-copper, palladium-lead, nickel-chromite.

The metal hydrogenation catalysts can be utilized with promoters that may or may not be other metals. Typical metal catalysts with promoter include, for example, nickel with sulfur or copper as promoter; copper with chromium or zinc as promoter; zinc with chromium as promoter; or palladium on carbon with silver or bismuth as promoter.

In one embodiment, a nickel catalyst that has been chemically reduced with hydrogen to an active state can be used as a hydrogenation catalyst. Commercial examples of supported nickel hydrogenation catalysts include those available under the trade names "Nysofact," "Nysosel," and "NI 5248 D" (ex Engelhard Corporation). Other supported nickel hydrogenation catalysts include those commercially available under the trade names "Pricat 9910," "Pricat 9920," "Pricat 9908" and "Pricat 9936" (ex Johnson Matthey).

The metal catalysts may be used as fine dispersions in a hydrogenation reaction (slurry phase environment). For example, in some embodiments, the particles of supported nickel catalyst are dispersed in a protective medium comprising hardened triacylglyceride, edible oil, or tallow. The supported nickel catalyst may be dispersed in the protective medium at a level of about 22 wt % nickel.

The hydrogenation catalysts may be impregnated on solid supports. Some useful supports include carbon, silica, alumina, magnesia, titania and zirconia. Examples of supported catalysts include palladium, platinum, rhodium or ruthenium on carbon or alumina support; nickel on magnesia, alumina or zirconia support; palladium on barium sulphate support; or copper on silica support.

The hydrogenation catalysts may be supported nickel or sponge nickel type catalysts. In some embodiments, the catalyst comprises nickel that has been chemically reduced with hydrogen to an active state (i.e. reduced nickel) provided on a support. The support may comprise porous silica (e.g. kieselguhr, infusorial, diatomaceous, or siliceous earth) or alumina. These catalysts can be characterized by a high nickel surface area per gram of nickel.

The supported nickel catalysts may be of the type described in U.S. Pat. No. 3,351,566, which comprise solid nickel-silica having a stabilized high nickel surface area of preferably 45 to 60 square meters per gram and a total surface area of 225 to 300 square meters per gram. These catalysts can be prepared by precipitating the nickel and silicate ions from solution such as nickel hydrosilicate onto porous silica particles in such proportions that the activated catalyst preferably comprises 25 to 50 wt % nickel and a total silica content of 30 to 90 wt %. The particles can be activated by calcining in air, e.g. at about 300° C. to about 500° C., and then reducing with hydrogen.

Useful catalysts having a high nickel content are described in EP-0168091, wherein the catalyst is made by precipitation of a nickel compound. A soluble aluminum compound is added to the slurry of the precipitated nickel compound while the precipitate is maturing. After reduction of the resultant catalyst precursor, the reduced catalyst typically has a nickel surface area of the order of 90 to 150 square meters per gram of total nickel. The catalysts preferably have a nickel/aluminum atomic ratio in the range of 2 to 10 and a total nickel content of more than about 66% by weight.

Useful high activity nickel/alumina/silica catalysts are described in EP-0167201. The reduced catalysts have a high nickel surface area per gram of total nickel in the catalyst.

Useful nickel/silica catalysts are described in U.S. Pat. No. 6,846,772. The catalysts are produced by heating a slurry of particulate silica (e.g. kieselguhr) in an aqueous nickel amine carbonate solution for a total period of at least 200 minutes at a pH above 7.5, followed by filtration, washing, drying, and optionally calcination. The nickel/silica hydrogenation catalysts are reported to have improved filtration properties. U.S. Pat. No. 4,490,480 describes high surface area nickel/alumina hydrogenation catalysts, preferably having a total nickel content of 5% to 40% by weight.

The hydrogenation catalyst is suitably used at a concentration of less than 10%, preferably less than 5%, more preferably less than 3%, particularly in the range from 0.5 to 2%, and especially 0.8 to 1.2% by weight based on the weight of starting material.

The yield of branched $C_{10}$-$C_{26}$ fatty acids produced according to the present invention is suitably greater than 65%, preferably greater than 70%, more preferably in the range from 75 to 98%, particularly 80 to 95%, and especially 85 to 90% by weight.

The yield of monobranched $C_{10}$-$C_{26}$ fatty acids produced according to the present invention is suitably greater than 60%, preferably greater than 65%, more preferably in the range from 70 to 95%, particularly 75 to 90%, and especially 80 to 85% by weight.

A composition produced according to the present invention comprises monobranched $C_{10}$-$C_{26}$ fatty acids which suitably comprise (i) greater than 75%, preferably greater than 83%, more preferably greater than 86%, particularly in the range from 88 to 95%, and especially 90 to 93% by weight of monobranched fatty acids, i.e. contain a single alkyl, generally methyl, side branch; and/or (ii) less than 6%, preferably less than 4%, more preferably less than 3%, particularly in the range from 0.5 to 2.5%, and especially 1 to 2% by weight of polybranched fatty acids, i.e. contain two or more alkyl, generally methyl, side branches, both based upon the total weight of the composition.

The weight ratio of monobranched fatty acids to polybranched fatty acids in the composition is suitably greater than 10:1, preferably greater than 20:1, more preferably in the range from 30 to 150:1, particularly 35 to 100:1, and especially 40 to 50:1.

In addition, the composition suitably comprises (i) less than 20%, preferably less than 15%, more preferably less than 12%, particularly less than 10%, and especially less than 7% by weight of linear fatty acids; and/or (ii) greater than 1%, preferably greater than 2%, more preferably greater than 3%, particularly greater than 4%, and especially greater than 5% by weight of linear fatty acids, based upon the total weight of the composition.

The concentration of lactones (branched and/or linear) in the composition is suitably less than 5%, preferably less than 3%, more preferably less than 2%, particularly in the range from 0.05 to 1.5%, and especially 0.1 to 1% by weight based upon the total weight of the composition.

A particular surprising feature of the present invention is that the above defined composition can be obtained by process steps comprising or consisting of (i) isomerisation, (ii) separation of isomerisation catalyst, and optional reuse of the zeolite, (iii) removal of polymeric fatty acids, (iv) hydrogenation, and (v) separation of hydrogenation catalyst. The order of the aforementioned steps is preferred, but may be varied.

The monobranched fatty acids preferably comprise alkyl side branches (attached directly to a carbon atom of the longest linear chain) which are methyl, ethyl, propyl, or mixtures thereof. In a preferred embodiment, (i) greater than 75, more preferably greater than 85, particularly in the range from 90 to 98, and especially 93 to 96 molar % of the side-branched groups are methyl groups; and/or (ii) less than 25, more preferably less than 15, particularly in the range from 2 to 10, and especially 4 to 7 molar % of the side-branched groups are ethyl and/or propyl groups, both based on the total amount of monobranched fatty acids.

The monobranched fatty acids suitably comprise $C_{12}$-$C_{24}$ fatty acids, preferably $C_{14}$-$C_{22}$ fatty acids, more preferably $C_{16}$-$C_{22}$ fatty acids, particularly $C_{18}$ or $C_{22}$ fatty acids, and especially $C_{18}$ fatty acids based on the total weight of fatty acids present. The monobranched fatty acids suitably comprise greater than 70%, preferably greater than 80%, more preferably greater than 90%, particularly greater than 95%, and especially greater than 98%, by weight of fatty acids falling within the aforementioned carbon chain ranges, based on the total weight of monobranched fatty acids present.

The composition comprising monobranched fatty acids preferably has an acid value (measured as described herein) in the range from 145 to 210, more preferably 160 to 205, particularly 175 to 200, and especially 185 to 195 mgKOH/g.

The composition comprising monobranched fatty acids preferably has a saponification value (measured as described herein) in the range from 165 to 220, more preferably 175 to 210, particularly 185 to 200, and especially 190 to 195 mg KOH/g.

The composition comprising monobranched fatty acids preferably has an unsaponifiable content (measured as described herein) of less than 10, more preferably less than 5, particularly in the range from 1.0 to 3, and especially 1.5 to 2 g/100 g.

The composition comprising monobranched fatty acids preferably has an iodine value (measured as described herein) of less than 3, more preferably less than 1, particularly in the range from 0.05 to 0.5, and especially 0.1 to 0.2 g iodine/100 g.

The composition comprising monobranched fatty acids preferably has a cloud point (measured as described herein) in the range from 15 to 35° C., more preferably 20 to 30° C., particularly 25 to 28° C., and especially 26 to 27° C.

The composition comprising monobranched fatty acids preferably has a solidification point (measured as described herein) in the range from 20 to 35° C., more preferably 25 to 32° C., particularly 27 to 30° C., and especially 28 to 29° C.

The composition comprising monobranched fatty acids preferably has a colour (measured as described herein) of less than 100, more preferably less than 50, particularly less than 40, and especially less than 25 Hazen units.

The invention is illustrated by the following non-limiting examples.

In this specification the following test methods have been used.

(i) Acid Value
The acid value was measured using the A.O.C.S. Official method Te1a-64 (Reapproved 1997), and expressed as the number of milligrams of potassium hydroxide required to neutralise the free fatty acids in one gram of sample.

(ii) Saponification Value
The saponification value was determined using the A.O.C.S. Official Method TI 1a-64 (1997) and is defined as the number of milligrams of potassium hydroxide which reacts with one gram of sample under the prescribed conditions.

(iii) Unsaponifiable Value
The unsaponifiable value was measured using the A.O.C.S. Official Method, Ca6b-53 (1989).

(iv) Iodine Value
The iodine value was determined by the Wijs method (A.O.C.S. Official Method Tg 1-64 (1993)) and expressed as the number of grams of iodine absorbed by 100 grams of sample under the defined test conditions.

(v) Cloud Point
The cloud point was measured according to the A.O.C.S. Official Method (Cc 6-25).

(Vi) Solidification Point
The solidification point was measured according to the (vii) Colour
Colour was determined using the Method of Colour Determination in Hazen Units (Pt-Co scale), ISO 2211 (1973).

(viii) Titre
Titre (or melting point) was measured according to A.O.C.S. Official Method, Tr1a-64 (1989).

(ix) Fatty Acid Composition
The fatty acid composition (chain length, saturated/unsaturated, linear/branched) was determined using gas chromatography, using the method ISO 5508:1990(E) Animal and vegetable fats and oils—Analysis by gas chromatography of methyl esters of fatty acids.

(x) Zeolite Activity
i) 1000 g high oleic sunflower fatty acid, 50 g fresh or regenerated zeolite, 3.75 g triphenyl phosphine and 10 g water were charged to a 1.8 liter autoclave. The reaction mixture was flushed 3 times with nitrogen and pressurized with nitrogen to 1 bar. The reaction mixture was heated to 260° C. After 6 hours the reaction mixture was cooled to 80° C. and filtered using filter paper. The resultant filtrate was analysed after microhydrogenation and the degree of conversion measured.

ii) The procedure in i) was repeated except that zeolite recovered from the first reaction mixture by filtration was used. This used zeolite could be used alone or with a certain amount of additional fresh or regenerated zeolite. The amount of triphenyl phosphine used was reduced to the same percentage amount as the percentage of fresh or regenerated zeolite used, e.g. when 40 g used zeolite and 10 g fresh zeolite was used, the amount of triphenyl phosphine added was 0.75 g (20% of the original amount). The time of reaction was 10 hours.

iii) The procedure in ii) was repeated except that zeolite recovered from the reaction mixture in ii) was used and the time of reaction was 12 hours.

iv) The procedure in iii) was repeated, except that zeolite recovered from the reaction mixture in iii) was used, for a total of y hours until the same rate of conversion (same % by weight of unsaturated fatty acid starting material that is reacted) as in iii) was achieved. The % retention of zeolite activity=12/y×100.

v) The procedure in iv) was further repeated a number of times using zeolite recovered from the previous step.

EXAMPLES

Example I 150 g K-Ferrierite (HSZ 720KOA, ex Tosoh) was mixed with 450 g water, and subsequently 50 g 37% HCl-solution was added. The suspension was stirred for 8 hours at 50-60° C. After filtration and washing (until the pH of the filtrate was neutral) of the resultant H-Ferrierite, the product was dried overnight at 120° C.

1000 g high oleic sunflower fatty acid, 50 g H-Ferrierite produced above, 3.75 g triphenyl phosphine and 10 g water were charged to a 1.8 liter autoclave. The reaction mixture was flushed 3 times with nitrogen and pressurized with nitrogen to 1 bar. The reaction mixture was heated to 260° C. After 6 hours, the reaction mixture was cooled to 80° C. and filtered using filter paper. The resultant filtrate was analysed and had the following composition;

| Component | % by Weight* |
|---|---|
| C14 branched | 0.3 |
| C16 branched | 0 |
| C18 poly branched | 3.2 |
| C18 mono branched | 70.0 |
| C20 branched | 1.6 |
| C22 branched | 0.2 |
| Linear C16 | 1.1 |
| Linear C18 | 9.6 |
| Lactones (branched+linear) | 6.9 |
| Dimer | 4.5 |
| Trimer | 0.1 |

*analysed after microhydrogenation.

The reaction product was then vacuum distilled to 230° C. to remove the dimer/trimer fraction.

Example 2

500 g of distilled product from Example 1 and 8.6 g hydrogenation catalyst were charged to a 2 liter autoclave. The reaction mixture was flushed 3 times with nitrogen and pressurized with hydrogen to 25 bar. The reaction mixture was heated to 230° C. After 10 hours the reaction mixture was cooled to 80° C. and optionally filtered through a silica gel column. The resultant filtrate was analysed and had the following composition;

| Component | % by Weight |
| --- | --- |
| C14 branched | 1.1 |
| C16 branched | 0.1 |
| C18 poly branched | 4.5 |
| C18 mono branched | 79.3 |
| C20 branched | 0.8 |
| C22 branched | 0 |
| Linear C16 | 2.2 |
| Linear C18 | 10.9 |
| Lactones (branched+linear) | 0.2 |

Example 3

1000 g erucic fatty acid, 50 g H-Ferrierite, 3.75 g triphenyl phosphine and 10 g water were charged to a 1.8 liter autoclave. The reaction mixture was flushed 3 times with nitrogen and pressurized with nitrogen to 1 bar. The reaction mixture was heated to 260° C. After 6 hours, the reaction mixture was cooled to 80° C. and filtered over a carton depth filter. The resultant filtrate was analysed and had the following composition;

| Component | % by Weight* |
| --- | --- |
| C16 branched | 0.3 |
| C18 branched | 0.3 |
| C20 branched | 6.2 |
| C22 poly branched | 3.1 |
| C22 mono branched | 65.3 |
| C24 branched | 2.7 |
| Linear C16 | 0.1 |
| Linear C18 | 0.1 |
| Linear C20 | 3.1 |
| Linear C22 | 8.5 |
| Lactones (branched+linear) | 6.3 |
| Dimer | 4.4 |
| trimer | 0.1 |

*analysed after microhydrogenation.

The reaction product was then vacuum distilled to 230° C. to remove the dimer/trimer fraction.

Example 4

500 g of distilled product from Example 3 and 8.6 g hydrogenation catalyst were charged to a 2 liter autoclave. The reaction mixture was flushed 3 times with nitrogen and pressurized with hydrogen to 25 bar. The reaction mixture was heated to 230° C. After 10 hours, the reaction mixture was cooled to 80° C. and optionally filtered through a silica gel column. The resultant filtrate was analysed and had the following composition;

| Component | % by Weight |
| --- | --- |
| C16 branched | 0.5 |
| C18 branched | 0.7 |
| C20 branched | 6.8 |
| C22 poly branched | 2.8 |
| C22 mono branched | 69.6 |
| C24 branched | 1.7 |
| Linear C16 | 0.5 |
| Linear C18 | 0.5 |
| Linear C20 | 2.0 |
| Linear C22 | 13.9 |
| Lactones (branched+linear) | 0.3 |

Example 5 i) 1000 g high oleic sunflower fatty acid, 50 g H-Ferrierite, 3.75 g triphenyl phosphine and 10 g water were charged to a 1.8 liter autoclave. The reaction mixture was flushed 3 times with nitrogen and pressurized with nitrogen to 1 bar. The reaction mixture was heated to 260° C. After 6 hours the reaction mixture was cooled to 80° C. and filtered using filter paper. The resultant filtrate was analysed and the degree of conversion measured.

ii) The procedure in i) was repeated except that 40 g H-Ferrierite recovered from the first reaction mixture by filtration and 10 g fresh H-Ferrierite were used. The amount of triphenyl phosphine added was 0.75 g and the time of reaction was 10 hours.

iii) The procedure in ii) was repeated except that 40 g H-Ferrierite recovered from the second reaction mixture by filtration and 10 g fresh H-Ferrierite were used. The amount of triphenyl phosphine added was 0.75 g and the time of reaction was 12 hours.

iv) The procedure in iii) was repeated several times. The resultant filtrates were analysed and the degree of conversion measured.

| | Fresh Catalyst | 1st reuse | 2nd reuse | 4th reuse | 6th reuse | 9th reuse |
| --- | --- | --- | --- | --- | --- | --- |
| Time of Reaction | 6 hours | 10 hours | 12 hours | 12 hours | 12 hours | 12 hours |
| Conversion Rate* | 91.6% | 93.1% | 92.8% | 92.1% | 91.9% | 91.4% |

*analysed after microhydrogenation.

The invention claimed is:

1. A process for producing monobranched fatty acids or alkyl esters thereof which comprises;
   (A) (i) isomerising unsaturated $C_{10}$-$C_{26}$ fatty acids or alkyl esters thereof in the presence of a catalyst which comprises both a zeolite and a Lewis base,
      (ii) separating the reaction product of step (i) from the used zeolite,
      (iii) optionally hydrogenating the reaction product of step (ii),
      (iv) obtaining a composition comprising monobranched $C_{10}$-$C_{26}$ fatty acids or alkyl esters thereof from the reaction product of step (ii) or (iii), and
   (B) wherein the process steps (A)(i) to (iv) are repeated using zeolite which comprises used zeolite which has been obtained in step (A)(ii).

2. The process according to claim 1 wherein step (B) occurs 5 or more times and the reused zeolite is obtained from the previous step (B).

3. The process according to claim 1 wherein the process is a batch or a continuous process.

4. The process according to claim 1 wherein the zeolite used in step B comprises fresh or regenerated zeolite.

5. The process according to claim 4 wherein the zeolite used in step B comprises 15 to 25% by weight of fresh or regenerated zeolite.

6. The process according to claim 1 wherein the amount of Lewis based used in step (B) is less than 80% by weight of the amount of Lewis base used in step (A).

7. The process according to claim 1 wherein the ratio of the amount of Lewis base used in step (A) to step (B) is 2 to 20:1.

8. The process according to claim 1 wherein the zeolite catalyst retains at least 95% of its activity after the third reuse.

9. The process according to claim 8 wherein the zeolite catalyst retains at least 95% of its activity after the fifth reuse.

10. The process according to claim 1 wherein the weight ratio of monobranched fatty acids or alkyl esters thereof to polybranched fatty acids or alkyl esters thereof in the composition obtained in step (A)(ii) or (iii) is greater than 20:1.

11. A composition comprising (i) greater than 70% by weight of monobranched $C_{10}$-$C_{26}$ fatty acids or alkyl esters thereof, (ii) less than 7% by weight of polybranched $C_{10}$-$C_{26}$ fatty acids or alkyl esters thereof, (iii) greater than 3% by weight of linear $C_{10}$-$C_{26}$ fatty acids or alkyl esters thereof, and (iv) less than 5% by weight of lactones, all based on the total weight of the composition.

12. A process comprising catalysing the isomerisation of unsaturated $C_{10}$-$C_{26}$ fatty acids or alkyl esters thereof to produce highly monobranched $C_{10}$-$C_{26}$ fatty acids or alkyl esters thereof in the presence of a catalyst which comprises both a zeolite and a Lewis base.

13. The process according to claim 12 wherein the monobranched fatty acids or alkyl esters thereof comprise greater than 75% by weight of monobranched fatty acids and less than 6% by weight of polybranched fatty acids.

14. The process according to claim 12 wherein the zeolite is reused.

15. A steady state process for producing $C_{10}$-$C_{26}$ monobranched fatty acids or alkyl esters thereof, comprising:
(i) isomerizing unsaturated $C_{10}$-$C_{26}$ fatty acids or alkyl esters thereof in a steady state process in the presence of a catalyst which comprises both a zeolite and a Lewis base;
(ii) separating the used zeolite from the reaction product of the isomerisation reaction, and
(iii) reusing the zeolite separated in step (i).

* * * * *